(12) United States Patent
Okamoto et al.

(10) Patent No.: US 12,337,128 B2
(45) Date of Patent: Jun. 24, 2025

(54) BALLOON CATHETER

(71) Applicant: GOODMAN CO., LTD., Aichi (JP)

(72) Inventors: Mitsumasa Okamoto, Aichi (JP); Mitsuhiro Ota, Aichi (JP); Soichiro Fujisawa, Aichi (JP); Masahiko Ohara, Aichi (JP); Keitaro Horiba, Aichi (JP); Takashi Kunisada, Aichi (JP)

(73) Assignee: Goodman Co., Ltd., Aichi (JP)

( * ) Notice: Subject to any disclaimer, the term of this patent is extended or adjusted under 35 U.S.C. 154(b) by 866 days.

(21) Appl. No.: 17/547,543

(22) Filed: Dec. 10, 2021

(65) Prior Publication Data

US 2022/0096804 A1 Mar. 31, 2022

Related U.S. Application Data

(63) Continuation of application No. PCT/JP2020/023416, filed on Jun. 15, 2020.

(30) Foreign Application Priority Data

Jun. 21, 2019 (JP) .................................. 2019-115743

(51) Int. Cl.
*A61M 25/10* (2013.01)
(52) U.S. Cl.
CPC . *A61M 25/1002* (2013.01); *A61M 2025/1004* (2013.01); *A61M 2025/1086* (2013.01)
(58) Field of Classification Search
CPC ...... A61M 25/1002; A61M 2025/1004; A61M 2025/1086; A61M 2025/109; A61M 25/104; A61M 25/10; A61M 25/0138; A61M 2025/1031; A61M 2025/105; A61M 25/0054; A61M 2025/006
See application file for complete search history.

(56) References Cited

U.S. PATENT DOCUMENTS

| | | | |
|---|---|---|---|
| 2003/0163148 | A1 | 8/2003 | Wang et al. |
| 2006/0106412 | A1 | 5/2006 | Crow et al. |
| 2006/0184191 | A1 | 8/2006 | O'Brien |

(Continued)

FOREIGN PATENT DOCUMENTS

| | | |
|---|---|---|
| CN | 108601929 A | 9/2018 |
| GB | 2487400 A | 7/2012 |

(Continued)

OTHER PUBLICATIONS

Extended European Search Report issued in corresponding European Patent Application No. EP 20825601.6 dated Jul. 11, 2022 (7 pages).

(Continued)

*Primary Examiner* — Bhisma Mehta
*Assistant Examiner* — Nelson Louis Alvarado, Jr.
(74) *Attorney, Agent, or Firm* — Osha Bergman Watanabe & Burton LLP

(57) ABSTRACT

A balloon catheter includes an inflatable balloon disposed on a tip-end side of the balloon catheter. A linear part of an outer surface of the inflatable balloon extends linearly in an axial direction of the inflatable balloon, the linear part has a notch at an intermediate position in a length direction of the linear part, and the notch opens in a direction intersecting the length direction.

6 Claims, 4 Drawing Sheets

(56) References Cited

U.S. PATENT DOCUMENTS

| | | |
|---|---|---|
| 2009/0192537 A1 | 7/2009 | O'Brien |
| 2011/0160756 A1 | 6/2011 | Aggerholm et al. |
| 2011/0264185 A1* | 10/2011 | Haslinger ............ A61M 25/104 264/293 |
| 2012/0191111 A1* | 7/2012 | Aggerholm .... A61B 17/320725 606/159 |
| 2013/0018396 A1 | 1/2013 | Gunderson et al. |
| 2018/0043140 A1 | 2/2018 | Iwano et al. |
| 2018/0200491 A1 | 7/2018 | Giasolli et al. |
| 2019/0091452 A1 | 3/2019 | Fujisawa et al. |

FOREIGN PATENT DOCUMENTS

| | | |
|---|---|---|
| JP | 2005-518842 A | 6/2005 |
| JP | 2008-529658 A | 8/2008 |
| JP | 2009-112361 A | 5/2009 |
| WO | 2017/204042 A1 | 11/2017 |

OTHER PUBLICATIONS

Office Action issued in counterpart Korean Application No. 10-2022-7002000, dated Mar. 20, 2024 (9 pages).
Office Action issued in counterpart Israeli Application No. 2888371, dated Apr. 7, 2024 (6 pages).
Office Action issued in counterpart Brazil Patent Application No. 112021025201-0 mailed Jun. 20, 2024 (9 pages).
Examination Report No. 1 issued in corrersponding Australian Application No. 2020298429 mailed Jul. 19, 2022 (5 pages).
Office Action issued in Corresponding Singapore Application No. 11202113272X, dated Sep. 4, 2024 (7 Pages).
Office Action issued in corresponding Indian Patent Application No. 202117054337 dated Sep. 19, 2022 (5 pages).
International Search Report issued in corresponding International Application No. PCT/JP2020/023416, mailed on Aug. 4, 2020 (5 pages).
Written Opinion issued in corresponding International Application No. PCT/JP2020/023416, mailed on Aug. 4, 2020 (3 pages).
Office Action issued in counterpart Japanese Patent Application No. JP 2021-528219 A, mailed May 9, 2023 (6 pages).
Office Action issued in corresponding Canadian Application No. 3,140,474, dated Aug. 28, 2023 (3 pages).
Office Action issued in corresponding Russian Application No. 2021135190, dated Sep. 13, 2023, with English translation (12 pages).
Office Action issued in corresponding Chinese Application No. 202080041681.X dated Jan. 19, 2023 (14 pages).
International Preliminary Report on Patentability issued in corresponding International Application No. PCT/JP2020/023416, mailed on Dec. 30, 2021 (10 pages).
Office Action issued in counterpart Indian Patent Application No. IN 202117054337 mailed Mar. 1, 2024 (3 pages).

* cited by examiner

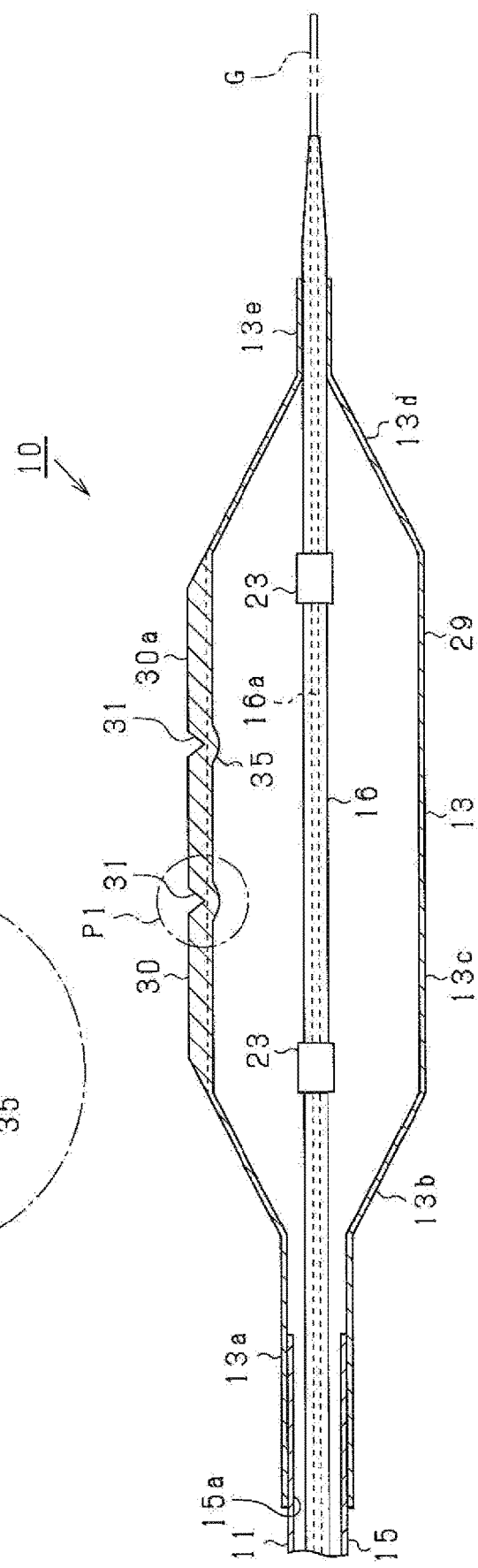
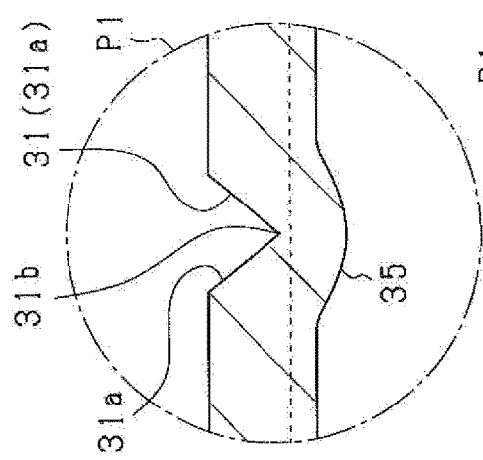
FIG. 2A
FIG. 2B

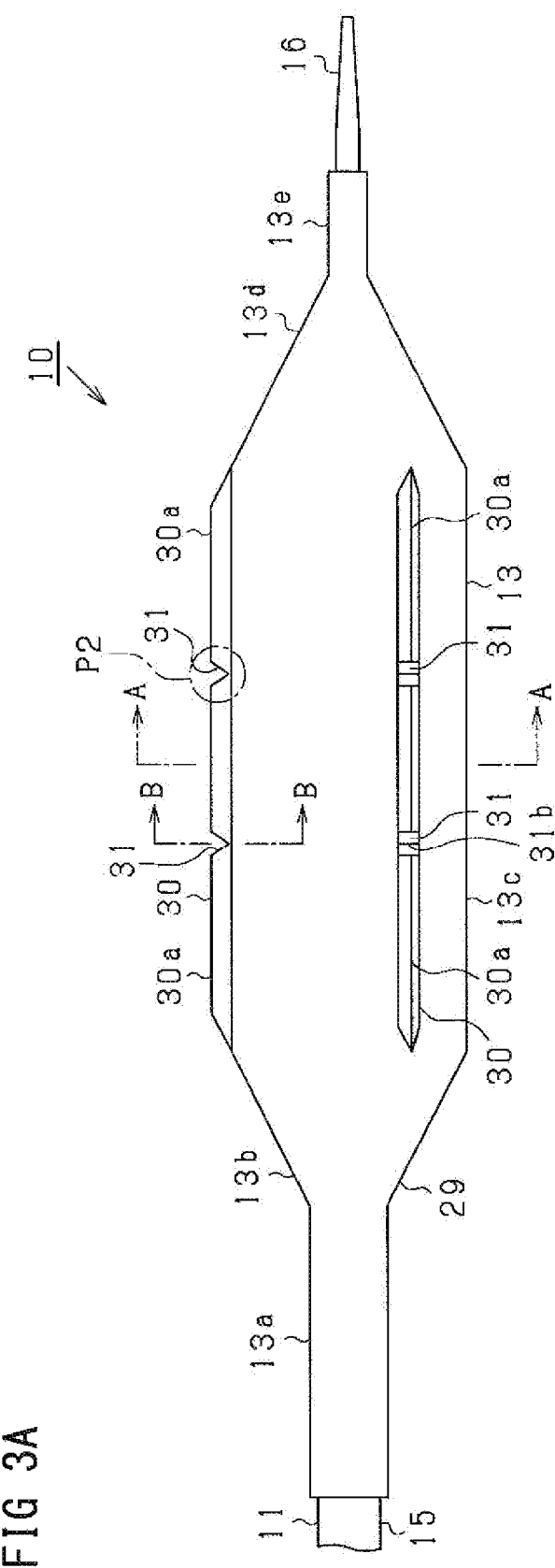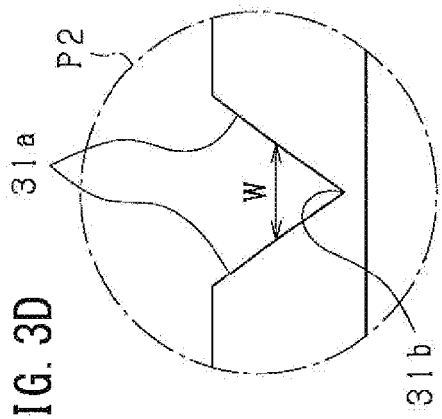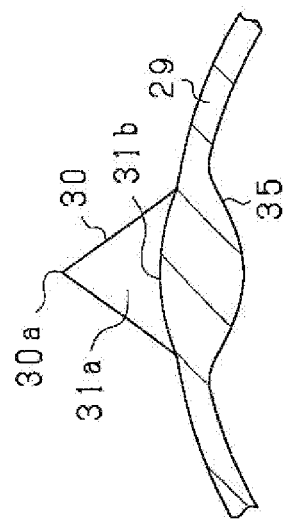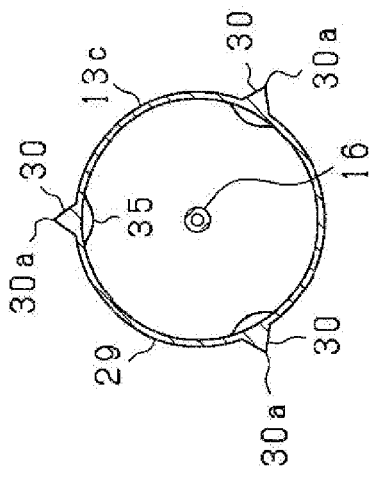

BALLOON CATHETER

CROSS-REFERENCE TO RELATED APPLICATION

The present application claims priority from Japanese Patent Application No. 2019-115743 filed on Jun. 21, 2019, the contents of which are incorporated herein by reference in their entirety.

BACKGROUND

Technical Field

The present disclosure relates to a balloon catheter.

Description of Related Art

A balloon catheter has been used for remedies such as PTA (percutaneous transluminal angioplasty) and PTCA (percutaneous transluminal coronary angioplasty), etc. The balloon catheter includes an inflatable and deflatable balloon on a tip-end side thereof. As for the balloon catheter, the balloon in a deflated state is introduced into a spot narrowed or obstructed by a lesion or the like produced in a blood vessel and then the spot is stretched by inflating the balloon.

Some balloon catheters are provided with a linear element extending in an axial direction to an outer surface of the balloon (for example, see Patent Literature 1). When the balloon is inflated in the lesion, the balloon catheter allows the element to make an incision in the lesion. This makes it easy to stretch the lesion.

Patent Literature

Patent Literature 1: Japanese Patent Laid-Open No. 2009-112361

Now, while the balloon catheter is being introduced into a blood vessel, the balloon may pass through a curved blood vessel on the way. Here, with the balloon catheter that includes the above-mentioned element, when the balloon passes through the curved blood vessel, it is conceivable that the element will stick out, disabling the balloon from properly following the curved blood vessel. This might make introduction work difficult due to an increase in resistance against the balloon being introduced into the body.

SUMMARY

One or more embodiments of the present disclosure provide a balloon catheter capable of curbing reduction in ease of operation when being introduced into the body.

A balloon catheter of a first aspect of one or more embodiments includes a balloon configured to be inflatable and deflatable and provided on a tip-end side, wherein: a linear part is formed in an outer surface of the balloon, extending linearly in an axial direction of the balloon; and a notch depressed in shape is formed in the linear part at an intermediate position in a length direction of the linear part, opening in a direction intersecting the length direction.

According to the present aspect, a linear part is formed in an outer surface of the balloon, extending in the axial direction of the balloon and a notch is formed at an intermediate position in the length direction of the linear part. This makes the linear part easily bendable starting at the notch and thereby curb reduction in trackability of the balloon with the linear part sticking out when the balloon is passed through a curved blood vessel. This makes it possible to curb reduction in ease of operation in introducing the balloon into the body.

According to a second aspect of one or more embodiments, in the balloon catheter according to the first aspect, the linear part is either formed integrally with the balloon or fixed to the outer surface of the balloon.

According to the present aspect, since the linear part is either formed integrally with the balloon or fixed to the outer surface of the balloon, when the balloon is inflated, the linear part is not displaced from the balloon. This makes it possible to make an incision suitably in a lesion with the linear part by inflating the balloon. However, with this configuration, it is assumed that the linear part tends to stick out more easily when the balloon is passed through a curved blood vessel. This greatly reduces trackability along the curved blood vessel, conceivably making the operation of introducing the balloon into the body more difficult. In this regard, according to the present aspect, since the first aspect is applied to the present configuration, reduction in ease of operation can be curbed suitably in introducing the balloon into the body even in the present configuration.

According to a third aspect of one or more embodiments, in the balloon catheter according to the first or second aspect, the notch is formed in such a position as to divide a length of the linear part into substantially equal parts.

According to the present aspect, since the notch is formed in such a position as to divide the length of the linear part into equal parts, the linear part can be suitably made easily bendable. This makes it possible to further curb reduction in trackability along a curved blood vessel.

According to a fourth aspect of one or more embodiments, in a balloon catheter according to any one of the first to third aspects, a width of the notch tapers down toward a bottom of the notch.

According to the present aspect, local changes in rigidity of the balloon catheter can be curbed at a location of the notch. This provides the effect of the first aspect while keeping kinking from occurring on the balloon catheter at the location of the notch.

According to a fifth aspect of one or more embodiments, in a balloon catheter according to any one of the first to fourth aspects, the balloon is formed of a film with a predetermined thickness; the linear part is formed integrally with the film; and a protrusion is formed on the film at a position corresponding to the notch, protruding to an inner circumferential side of the balloon.

According to the present aspect, the linear part is formed integrally with the film that forms the balloon. With this configuration, it is considered that in introducing the balloon into a curved blood vessel, when the balloon (in other words, the film) compliantly deforms starting at the notch in the linear part, stress resulting from the compliant deformation tends to concentrate on the spot corresponding to the notch in the film part. Therefore, it is feared that disadvantages such as elongation of the film may occur at this spot.

Thus, in view of the above point, according to the present aspect, a protrusion is formed on the film at a position corresponding to the notch in the linear part, protruding to the inner circumferential side of the balloon. In this case, the film is increased in thickness at the location of the notch, making it possible to increase strength of the film. This in turn makes it possible to limit the disadvantages described above.

BRIEF DESCRIPTION OF DRAWINGS

The above and other features and advantages of one or more embodiments of the present disclosure will become more apparent from the following detailed description when taken in conjunction with the accompanying drawings.

FIG. 2A is a side view of a balloon in an inflated state and a vicinity thereof, showing the balloon and an outer tube in a longitudinal cross section and FIG. 2B is a partial enlarged view showing a part P1 in FIG. 2A.

FIG. 3A is a side view showing a configuration of the balloon in the inflated state and the vicinity thereof, FIG. 3B is a cross sectional view taken along line A-A in FIG. 3A, FIG. 3C is a cross-sectional view taken along line B-B in FIG. 3A, and FIG. 3D is a partial enlarged view showing a part P2 in FIG. 3A.

DETAILED DESCRIPTION OF EMBODIMENTS

Figure 1:
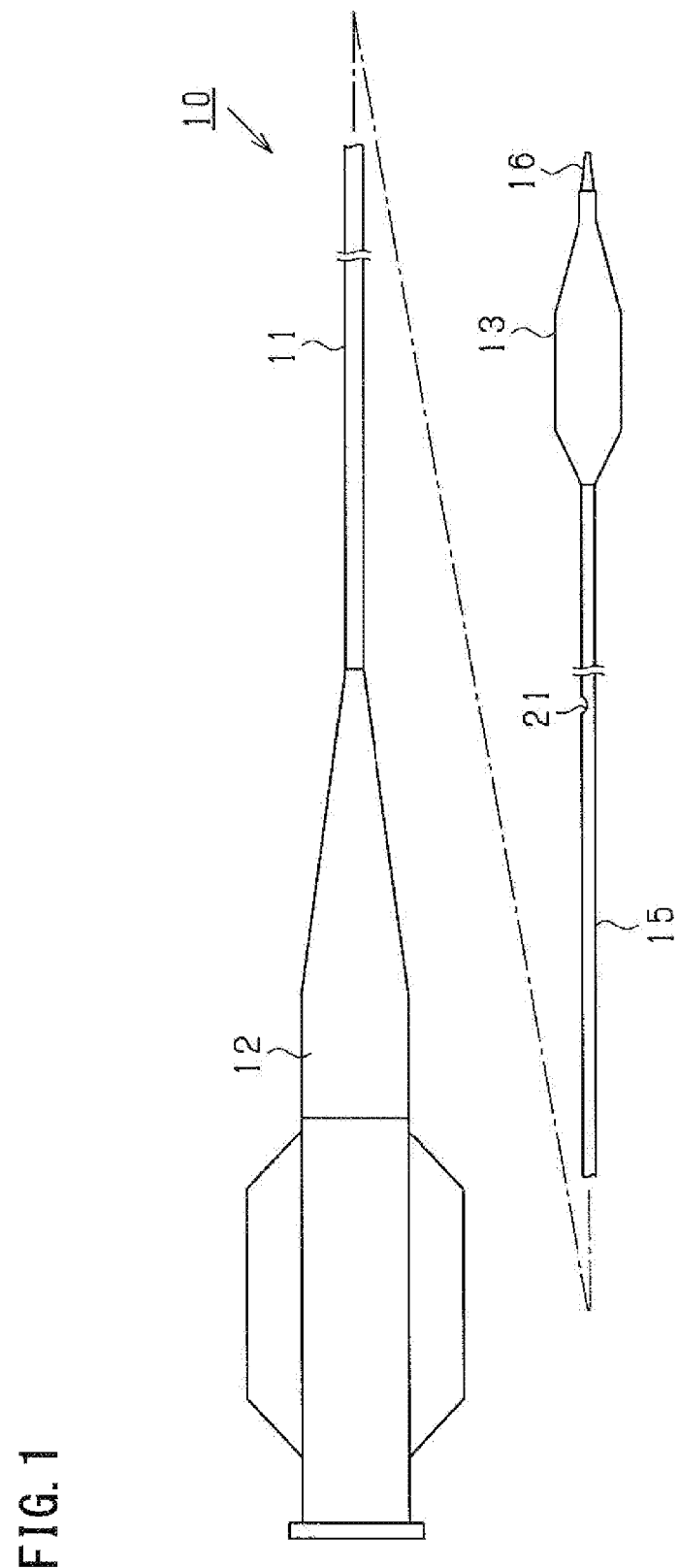
FIG. 1 is a schematic overall side view showing a configuration of a balloon catheter.

Embodiments of a balloon catheter will be described below based on the drawings. First, a schematic configuration of a balloon catheter 10 will be described with reference to FIG. 1. FIG. 1 is a schematic overall side view showing a configuration of the balloon catheter 10.

As shown in FIG. 1, the balloon catheter 10 includes a catheter body 11, a hub 12 attached to a base-end portion (proximal-end portion) of the catheter body 11, and a balloon attached on a tip-end side (distal-end side) of the catheter body 11.

The catheter body 11 includes an outer tube 15, and an inner tube 16 inserted in the outer tube 15. The outer tube 15 is formed of a resin material such as polyamide elastomer. The outer tube 15 is bonded to the hub 12 in a base-end portion, and to the balloon 13 in a tip-end portion. Besides, the outer tube 15 has a lumen 15a (see FIG. 2A) inside extending all through the outer tube 15 in the axial direction. The lumen 15a is communicated into the hub 12 as well as into the balloon 13.

Note that the outer tube 15 may be formed by bonding together plural tubes aligned in the axial direction. In this case, it is conceivable, for example, that those of the tubes which are on a base-end side are formed of a metal material such as a Ni—Ti alloy or stainless steel and those of the tubes which are on a tip-end side are formed of a resin material such as polyamide elastomer.

The inner tube 16 is formed of a resin material such as polyamide elastomer. The inner tube 16 has a lumen 16a (see FIG. 2A) inside extending all through the inner tube 16 in the axial direction. A base-end portion of the inner tube 16 is bonded to the outer tube 15 at an intermediate position of the outer tube 15 in the axial direction while part of the inner tube 16 on the tip-end side extends farther than the outer tube 15 to the tip-end side. Then, the balloon 13 is provided on the inner tube 16, externally covering the extended region.

The lumen 15a in the outer tube 15 functions as a fluid lumen through which a compressed fluid flows in inflating or deflating the balloon 13. Meanwhile, the lumen 16a in the inner tube 16 functions as a guide wire lumen through which a guide wire G is inserted. A base-end opening 21 of the lumen 16a is provided at an intermediate position of the balloon catheter 10 in the axial direction. Thus, the present balloon catheter 10 is a so-called RX catheter. Note that the base-end opening 21 of the lumen 16a may be in a base-end portion of the balloon catheter 10. In this case, the balloon catheter 10 is a so-called over-the-wire catheter.

Figure 4A:
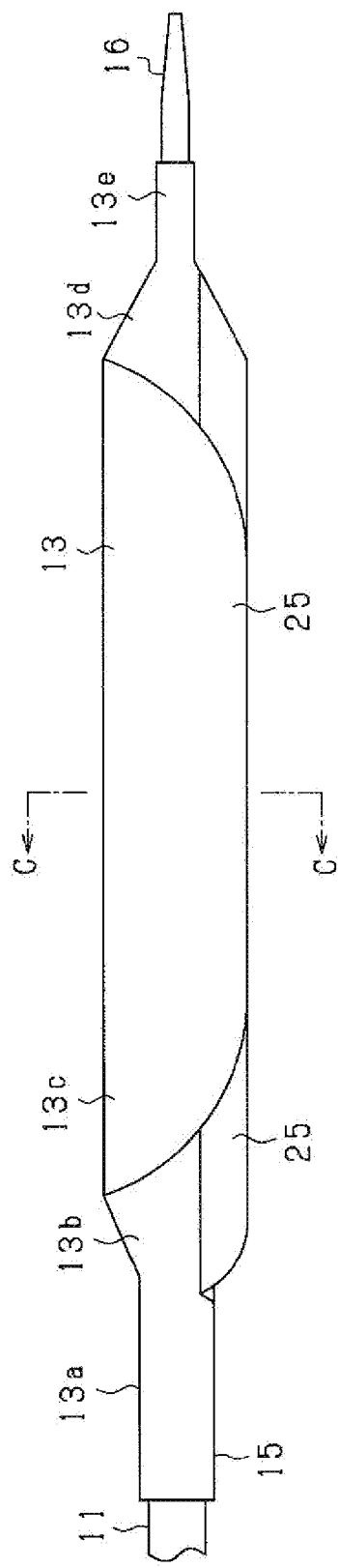
FIG. 4A is a side view showing a configuration of the balloon in a deflated state and the vicinity thereof and FIG. 4B is a cross sectional view taken along line C-C in FIG. 4A.
Figure 4B:
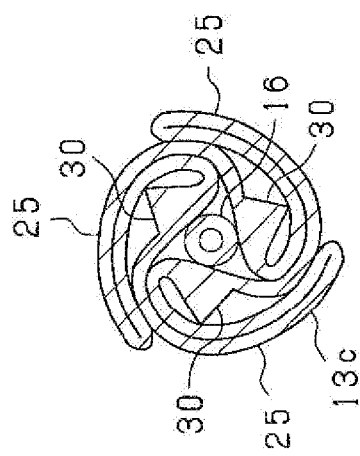

Next, a configuration of the balloon 13 and a vicinity thereof will be described based on FIG. 2 to FIG. 4. FIG. 2A is a side view of the balloon 13 in an inflated state and the vicinity thereof, showing the balloon 13 and the outer tube 15 in a longitudinal cross section and FIG. 2B is a partial enlarged view showing a part P1 in FIG. 2A. FIG. 3A is a side view showing a configuration of the balloon 13 in the inflated state and the vicinity thereof, FIG. 3B is a cross sectional view taken along line A-A in FIG. 3A, FIG. 3C is a cross-sectional view taken along line B-B in FIG. 3A, and FIG. 3D is a partial enlarged view showing a part P2 in FIG. 3A. FIG. 4A is a side view showing a configuration of the balloon 13 in a deflated state and the vicinity thereof and FIG. 4B is a cross sectional view taken along line C-C in FIG. 4A.

As described above, the balloon 13 is provided on the inner tube 16, externally covering the extended region, which extends farther than the outer tube 15 to the tip-end side. As shown in FIG. 2A and FIG. 3A, a base-end portion of the balloon 13 is bonded to a tip-end portion of the outer tube 15 while a tip-end portion of the balloon 13 is bonded to a tip-end side of the inner tube 16.

The balloon 13 is made of a thermoplastic polyamide elastomer. However, the balloon 13 may be formed of any thermoplastic resin other than polyamide elastomer as long as the balloon 13 can be properly inflated and deflated along with the supply and discharge of the fluid. For example, the balloon 13 may be formed of polyethylene, polyethylene terephthalate, polypropylene, polyurethane, polyamide, polyimide, polyimide elastomer, silicone rubber, or the like.

The balloon 13 is formed of a film 29 with a predetermined thickness. The balloon 13 includes bonding parts located at opposite ends and bonded to the catheter body 11, and an inflation/deflation portion provided between the bonding parts in order to be inflated and deflated. Specifically, the balloon 13 includes: a base-end leg region 13a bonded to the tip-end portion of the outer tube 15; a base-end cone region 13b tapered such that the inner diameter and outer diameter of the balloon 13 will increase continuously toward the tip-end side; a straight tube region 13c having constant inner and outer diameters throughout its length and serving as a maximum outer diameter region of the balloon 13; a tip-end cone region 13d tapered such that the inner diameter and outer diameter of the balloon 13 will decrease continuously toward the tip-end side; and a tip-end leg region 13e bonded to the tip-end side of the inner tube 16, which are arranged in this order from the base-end side. In this case, the base-end cone region 13b, the straight tube region 13c, and the tip-end cone region 13d make up the inflation/deflation portion while the base-end leg region 13a and the tip-end leg region 13e make up the bonding parts, respectively.

The balloon 13 becomes inflated when the compressed fluid is supplied into the balloon 13 through the lumen 15a of the outer tube 15 and becomes deflated when a negative pressure is applied to the lumen 15a, causing the compressed fluid to be discharged out of the balloon 13. As shown in FIGS. 4A and 4B, the balloon 13 includes plural (three according to the present embodiment) wings 25 formed in the deflated state. The wings 25 are provided at predetermined intervals (specifically, at regular intervals) in a circumferential direction of the balloon 13. The wings 25 are formed extending in the axial direction in the inflation/deflation portion of the balloon 13. In this case, the wings 25 extend across the base-end cone region 13b, the straight tube region 13c, and the tip-end cone region 13d. When the balloon 13 becomes deflated, the wings 25 are folded in the circumferential direction of the balloon 13, wrapping around the inner tube 16.

Note that a pair of contrast rings 23 are attached to the inner tube 16 inside the balloon 13. The contrast rings 23 are intended to improve the visibility of the balloon 13 during x-ray projection in order to position the balloon 13 easily with respect to a targeted treatment area.

A linear part 30 is provided on an outer surface of the balloon 13, extending linearly in an axial direction of the balloon 13. The linear part 30 is provided projecting from the outer surface of the balloon 13. The linear part 30 is used to make an incision in a lesion when the lesion is stretched by inflating the balloon 13. Even if a lesion has hardened due to calcification or the like, by making an incision in the lesion using the linear part 30, the present balloon catheter 10 can destroy the lesion using the incision as a starting point and make the lesion easily stretchable. Therefore, the present balloon catheter 10 has been configured as a so-called cutting balloon catheter (also referred to as a scoring balloon catheter).

As shown in FIGS. 2A, 3A, and 3B, the linear part 30 is provided in the straight tube region 13c of the balloon 13. The linear part 30 extends in the axial direction of the balloon 13 along an outer surface of the film 29 (i.e., an outer surface of the straight tube region 13c), and specifically, extends continuously in the axial direction across the entire straight tube region 13c. Plural linear parts 30 are placed at predetermined intervals (specifically, at regular intervals) in the circumferential direction of the balloon 13, and three linear parts 30 are placed at 120-degree intervals according to the present embodiment. Besides, the linear parts 30 are formed integrally with the film 29 (i.e., the balloon 13). Note that according to the present embodiment, the linear parts 30 have the same configuration.

All the linear parts 30 are triangular in transverse section (specifically, cross section orthogonal to a length direction of the linear parts 30). Each of the linear parts 30 is placed in such an orientation that one of the corners 30a thereof projects toward an outer circumferential side (outer side in the radial direction) of the balloon 13. Note that the linear parts 30 do not necessarily have to be triangular in transverse section, but may have another shape such as a semicircular shape or a rectangular shape in transverse section.

When the balloon 13 is deflated, the plural wings 25 are formed in the inflation/deflation portion (the straight tube region 13c and the cone regions 13b and 13d) of the balloon 13 and the wings 25 are folded in the circumferential direction of the balloon 13 as described above. In this case, as shown in FIGS. 4A and 4B, the linear parts 30 of the straight tube region 13c, which are provided in a one-to-one relationship with the wings 25, are placed inside the respective folded wings 25. This causes the linear parts 30 to be covered externally by the wings 25 when the balloon 13 is deflated—specifically, the linear parts 30 are entirely covered by the wings 25.

Here, with the present balloon catheter 10, notches 31 are provided in the respective linear parts 30. The present balloon catheter 10 is characterized by this and this characteristic configuration will be described below.

As shown in FIGS. 2A and 2B the notches 31 are formed in each of the linear parts 30 at intermediate positions in the length direction of the linear part 30. Plural (specifically, two) notches 31 are formed at predetermined intervals in each of the linear parts 30. Specifically, in each of the linear parts 30, the notches 31 are formed in such positions as to divide the length of the linear part 30 into three approximately equal parts. Therefore, the linear parts 30 have the same positional relationship between the notches 31 in the length direction of the linear parts 30 (in other words, in the axial direction of the balloon 13). Consequently, among the linear parts 30, the notches 31 are arranged side by side in the circumferential direction of the balloon 13. Note that according to the present embodiment, all the notches 31 in the linear parts 30 have the same configuration.

The notches 31 are formed only in such positions as to divide the length of each linear part 30 into three approximately equal parts, and are not formed in other positions. Consequently, a projection height (specifically, a projection height from the outer surface of the film 29) of each linear part 30 is constant throughout the entire linear part 30 except where the notches 31 are formed. In the areas where the notches 31 are formed, the projection height is lower than the constant height. Note that the projection height of the linear part 30 becomes minimal in areas where bottoms 31b of the notches 31 are formed. That is, the linear part 30 exists with the minimal projection height even at the bottoms 31b of the notches 31, and consequently the linear part 30 is formed continuously by crossing over the notches 31.

Each of the notches 31 has been formed into a depressed shape opening in a direction intersecting (specifically, a direction orthogonal to) the length direction of the linear part 30. Specifically, the notch 31 has been formed into a depressed shape opening to the side opposite the outer surface of the balloon 13 (in other words, to the outer side in the radial direction of the balloon 13). The notch 31 penetrates the linear part 30 in the circumferential direction of the balloon 13, opening to opposite sides in the circumferential direction. The notch 31 is triangular in shape—specifically, triangular as viewed in the circumferential direction of the balloon 13. According to the present embodiment, the notch 31 has a substantially equilateral triangular shape.

As shown in FIG. 3D, side faces 31a of the notch 31 opposed to each other, i.e., side faces 31a facing the length direction of the linear part 30, are inclined with respect to the length direction of the linear part 30 in such a way as to approach each other toward the bottom 31b of the notch 31. Consequently, a distance between the side faces 31a in the length direction of the linear part 30, i.e., a width W of the notch 31, decreases continuously toward the bottom 31b of the notch 31.

As shown in FIGS. 2B and 3C, protrusions 35 are formed on the film 29 of the balloon 13 at positions corresponding to the notches 31, protruding to an inner circumferential side (inner side) of the balloon 13. The protrusions 35 are provided together with the notches 31 in a thickness direction of the film 29. Consequently, at the positions corresponding to the notches 31, the film 29 is increased in thickness by the protrusions 35. Each of the protrusions 35 is curved convexly toward the inner circumferential side of the balloon 13 and has a substantially circular shape when viewed from the inner circumferential side of the balloon 13. Lengths of the protrusion 35 both in the axial direction and circumferential direction of the balloon 13 are substantially equal to or larger than a maximum width of the notch 31 (specifically, a width of an opening of the notch 31, where the opening faces the side opposite an outer circumferential surface of the balloon 13).

Next, a manufacturing method for manufacturing the balloon 13 will be described briefly.

First, a tubular parison, which is to be made into the balloon 13, is produced by extrusion molding. The tubular parison is formed in the shape of a circular tube, and ridges are formed on an outer circumferential surface of the tubular parison, extending in the axial direction. Plural (specifically, three) ridges, each of which has a triangular transverse section, are formed at regular intervals in a circumferential direction of the tubular parison.

Subsequently, the tubular parison is stretched in a length direction and then blow-molded under predetermined conditions using a mold with a cavity corresponding to the shape of the balloon 13. The mold has grooves formed to hold the ridges. Shallow portions with reduced groove depth are provided in part of the grooves in a length direction. The shallow portions are provided in such positions as to divide the length of each groove into three equal parts.

During blow-molding, the tubular parison is placed in the cavity with the ridges being held in the respective grooves of the mold and is blow-molded in this state. During the blow-molding, the tubular parison is expanded thermally in the mold (cavity). As a result of the blow-molding, the tubular parison becomes biaxially stretched and the ridges are formed into the respective linear parts 30. Then, the notches 31 are formed in those parts of the ridges which were placed in the shallow-groove portions. Subsequently, opposite ends of the stretched tubular parison are cut off, thereby completing the manufacturing of the balloon 13.

The above is a description of the manufacturing method of the balloon 13. Note that the manufacturing method of the balloon 13 is not necessarily limited to the above method, but another manufacturing method may be adopted.

Next, a method for using the balloon catheter 10 will be described. Here, description will be given of procedures for using the balloon catheter 10 to stretch a lesion produced in a blood vessel.

First, a guiding catheter is inserted through a sheath introducer inserted in a blood vessel and a tip-end opening of the guiding catheter is introduced into a coronary ostium. Next, the guide wire G is inserted through the guiding catheter and the inserted guide wire G is introduced from the coronary ostium to a peripheral site via the lesion.

Subsequently, the balloon catheter 10 is introduced into the guiding catheter along the guide wire G. Then, the balloon 13 is introduced into (positioned at) the lesion by push/pull operation. Note that while being introduced, the balloon 13 is kept deflated.

When the balloon 13 is introduced into the lesion, it is conceivable that the balloon 13 will pass through a curved blood vessel in the process of the introduction. In this case, with the present balloon 13, the linear parts 30, which are provided with the notches 31, are easily bendable starting at the notches 31. This makes it possible to curb reduction in trackability of the balloon 13 with the linear parts 30 sticking out when the balloon 13 is passed through the curved blood vessel. This in turn makes it possible to curb reduction in ease of operation in introducing the balloon 13 into the lesion.

Once the balloon 13 reaches the lesion, the balloon 13 is inflated. Consequently, the linear part 30 is pressed against the lesion, making incisions (producing cracks) in the lesion using the linear parts 30. This makes it possible to destroy the lesion using the incisions as a starting point and thereby make the lesion stretch outward.

Once the lesion is stretched by the balloon 13, the balloon 13 is deflated. Then, with the balloon 13 kept deflated, the balloon catheter 10 is pulled out of the body. This completes a series of operations.

Note that whereas the balloon catheter 10 is used for treatment of blood vessels such as the coronary arteries, the femoral arteries, or the pulmonary arteries by being passed mainly through the blood vessels as described above, the balloon catheter 10 can be used for "vessels" in a living body, such as the ureter or the gastrointestinal tract, other than blood vessels, as well as for "body cavities."

The configuration of the present embodiment described in detail above achieves the following excellent effects.

With the configuration in which the linear parts 30 are formed integrally with the balloon 13 (the film 29), when the balloon 13 is inflated, the linear parts 30 are not displaced from the balloon 13. This makes it possible to make incisions suitably in a lesion with the linear parts 30 by inflating the balloon 13. However, with this configuration, it is assumed that the linear parts 30 tend to stick out more easily when the balloon 13 is passed through a curved blood vessel. This might greatly reduce trackability along the curved blood vessel, making the operation of introducing the balloon 13 into the body more difficult. In this regard, according to the above embodiment, since the notches 31 are provided in the linear parts 30 in the present configuration, reduction in ease of operation can be curbed suitably in introducing the balloon 13 into the body even in the present configuration.

Plural notches 31 (n notches) are formed in such positions as to divide the length of each linear part 30 into substantially equal parts (n+1 parts). Specifically, two (n=2) notches 31 are formed in such positions as to divide the length of each linear part 30 into three approximately equal parts. In this case, since the linear parts 30 can be suitably made easily bendable, reduction in trackability along a curved blood vessel can be curbed further.

Since the width W of each notch 31 tapers down toward the bottom 31b of the notch 31 local changes in rigidity of the balloon catheter 10 can be curbed at the location of the notch 31. Consequently, the effects described above can be achieved by the notches 31 while keeping kinking from occurring on the balloon catheter 10 at the location of the notch.

With the configuration in which the linear parts 30 are formed integrally with the film 29 making up the balloon 13, it is considered that in introducing the balloon 13 into a curved blood vessel, when the balloon 13 (in other words, the film 29) compliantly deforms starting at the notches 31 in the linear parts 30, stress resulting from the compliant deformation tends to concentrate on the spots corresponding to the notches 31 in the film 29. Therefore, it is feared that disadvantages such as elongation of the film 29 may occur at these spots.

Thus, in the above embodiment, in view of this point, protrusions 35 are formed on the film 29 at positions corresponding to the notches 31 in the linear parts 30, protruding to the inner circumferential side of the balloon 13. In this case, the film 29 is increased in thickness at the locations of the notches 31, making it possible to increase strength of the film 29. This in turn makes it possible to limit the disadvantages described above.

Although the effects described above can be achieved by uniformly (generally) increasing the film 29 in thickness, flexibility of the balloon 13 might be impaired greatly in that case. In that regard, when the protrusions 35 are formed on the film 29 (only) at positions corresponding to the notches 31 as described above, the effects described above can be achieved while keeping the flexibility of the balloon 13 from being impaired greatly.

The present disclosure is not limited to the above embodiments, but may be implemented, for example, as follows.

Whereas in the above embodiment, the notch 31 has a triangular shape, the notch 31 may have another shape such as a semicircular shape or a rectangular shape.

Whereas in the above embodiment, the notches 31 are each formed into a depressed shape opening to the side opposite the outer circumferential surface of the balloon 13, the notches may each be formed into a depressed shape opening in the circumferential direction of the balloon 13. In this case, as notches, one or both of first notches opening to one side in the circumferential direction of the balloon 13 and second notches opening to the other side may be provided in the linear parts 30. For example, when both the first notches and second notches are provided in the linear parts 30, the notches may be provided at the same positions in the length direction of the linear parts 30. In this case, the first notches and the second notches are provided so as to open to sides opposite to each other.

Whereas in the above embodiment, two notches 31 are formed in each linear part 30, three or more notches 31 may be formed in each linear part 30. Alternatively, only one notch 31 may be formed in each linear part 30. In these cases, again, desirably the notches 31 are formed in such positions as to divide the length of the linear part 30 into equal parts. That is, when three notches 31 are formed, desirably the notches 31 are formed in such positions as to divide the length of the linear part 30 into four approximately equal parts. When only one notch 31 is formed, desirably the notch 31 is formed in such a position as to divide the length of the linear part 30 into two approximately equal parts, i.e., in substantially the center position of the linear part 30.

It is not strictly necessary to form the notches 31 in such positions as to divide the length of the linear part 30 into equal parts. For example, when only one notch 31 is formed, the notch 31 may be formed on the base-end side or tip-end side of the center of the linear part 30.

Whereas in the above embodiment, the linear parts 30 are formed integrally with the balloon 13, the linear parts may be formed separately from the balloon 13 and fixed to the outer surface of the balloon 13 by heat welding, bonding, or the like. In this case, again, effects similar to those of the above embodiment can be achieved by providing notches in the linear parts.

The linear parts may be formed separately from the balloon 13 and provided on the outer surface of the balloon 13 without being fixed. Specifically, in this case, the linear parts are formed of a resin material having elasticity and provided along the axial direction on the outer circumferential side of the balloon 13 by straddling the balloon 13. In so doing, the linear parts have their base-end portions bonded to the outer tube 15 and their tip-end portions bonded to the base-end portion of the inner tube 16. With this configuration, when the balloon 13 is inflated, the linear parts are placed on the outer surface of the balloon 13, extending in the axial direction. In so doing, the linear parts are placed on the outer surface of the balloon 13, projecting therefrom, and thus with this configuration, again, when the balloon 13 is inflated, incisions can be made in a lesion with the linear parts. With this configuration, again, effects similar to those of the above embodiment can be achieved by providing notches in the linear parts.

Whereas in the above embodiment, the linear parts 30 are provided (only) in the straight tube region 13c of the balloon 13, the linear parts 30 may be provided extending across the base-end cone region 13b and the tip-end cone region 13d in addition to being provided in the straight tube region 13c. In this case, the linear parts 30 are formed extending continuously in the axial direction along outer surfaces of the regions 13b to 13d. Alternatively, the linear parts 30 may be provided continuously all across the regions 13b to 13d in the axial direction.

Alternatively, the linear parts 30 may be provided extending over either one of the base-end cone region 13b and the tip-end cone region 13d in addition to being provided in the straight tube region 13c.

Whereas in the above embodiment, the linear parts 30 are used to make incisions in a lesion, the linear parts 30 may be used for other purposes. For example, the linear parts 30 may be used to provide slip resistance by inflating the balloon 13 in a blood vessel, causing the linear parts 30 to bite into a blood vessel wall, and thereby preventing the balloon 13 from slipping.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

REFERENCE SIGNS LIST

10 . . . balloon catheter, 13 . . . balloon, 13c . . . straight tube region, 29 . . . film, 30 . . . linear part, 31 . . . notch, 35 . . . protrusion

What is claimed is:

1. A balloon catheter comprising:
   an inflatable balloon disposed on a tip-end side of the balloon catheter, wherein
   the inflatable balloon includes a linear part that protrudes from an outer surface of the inflatable balloon and linearly extends in an axial direction of the inflatable balloon,
   the linear part has a notch at an intermediate position in a length direction of the linear part,
   the notch opens in a direction intersecting the length direction,
   the inflatable balloon is formed of a film having a predetermined thickness,
   the linear part is formed integrally with the film,
   the film has a protrusion at a position corresponding to the notch,
   the protrusion protrudes to an inside of the inflatable balloon, and
   the film is increased in thickness by the protrusion at the position corresponding to the notch.

2. The balloon catheter according to claim 1, wherein the notch divides a length of the linear part into parts of equal lengths.

3. The balloon catheter according to claim 1, wherein the notch has a width that tapers to a bottom of the notch.

4. A balloon catheter comprising:
   an inflatable balloon disposed on a tip-end side of the balloon catheter, wherein
   the inflatable balloon includes a linear part that protrudes from an outer surface of the inflatable balloon and linearly extends in an axial direction of the inflatable balloon,
   the linear part has a notch at an intermediate position in a length direction of the linear part,
   the notch opens in a direction intersecting the linear part, the inflatable balloon is formed of a film that is formed integrally with the linear part, the film has a protrusion at a position corresponding to the notch, the protrusion protrudes to an inside of the inflatable balloon, and the film includes a portion that includes the protrusion and has a thickness greater than a thickness of another portion of the film.

5. The balloon catheter according to claim 4, wherein the notch divides a length of the linear part into parts of equal lengths.

6. The balloon catheter according to claim 4, wherein the notch has a width that tapers to a bottom of the notch.

* * * * *